US00PP15465P3

(12) United States Plant Patent
Ligonniere

(10) Patent No.: US PP15,465 P3
(45) Date of Patent: Jan. 4, 2005

(54) APPLE TREE NAMED 'DALITOGA'

(50) Latin Name: *Malus domestica Mill.*
Varietal Denomination: Dalitoga

(75) Inventor: Guy Raymond Ligonniere, Angers (FR)

(73) Assignee: SNC Elaris, Angers (FR)

( * ) Notice: Subject to any disclaimer, the term of this patent is extended or adjusted under 35 U.S.C. 154(b) by 0 days.

(21) Appl. No.: 10/639,179

(22) Filed: Aug. 11, 2003

(65) Prior Publication Data

US 2004/0034891 P1 Feb. 19, 2004

(30) Foreign Application Priority Data

Aug. 13, 2002 (QZ) ..... PBR 2002/1259

(51) Int. Cl.[7] ..... A01H 5/00

(52) U.S. Cl. ..... Plt./162

(58) Field of Search ..... Plt./162

*Primary Examiner*—Kent Bell
(74) *Attorney, Agent, or Firm*—Stratton Ballew PLLC

(57) ABSTRACT

A new and distinct Gala-type apple cultivar is disclosed. The new cultivar 'Dalitoga' arose as a whole tree mutation of 'Imperial Gala.' 'Dalitoga' is notable for its intense coloration and early maturity as compared to its parent and to other known Gala cultivars.

7 Drawing Sheets

Latin name of the genus and species of the plant claimed: *Malus domestica* Mill.
Variety denomination: 'Dalitoga'.

CROSS REFERENCE TO RELATED APPLICATIONS

None.

PRIORITY CLAIM

This application claims priority under 35 U.S.C. §119(f) of European Plant Variety Rights application Ser. No. 2002/1259 filed Aug. 13, 2002.

STATEMENT REGARDING FEDERALLY SPONSORED RESEARCH OR DEVELOPMENT

None.

BRIEF DESCRIPTION OF THE PHOTOGRAPHS

Figure 1:
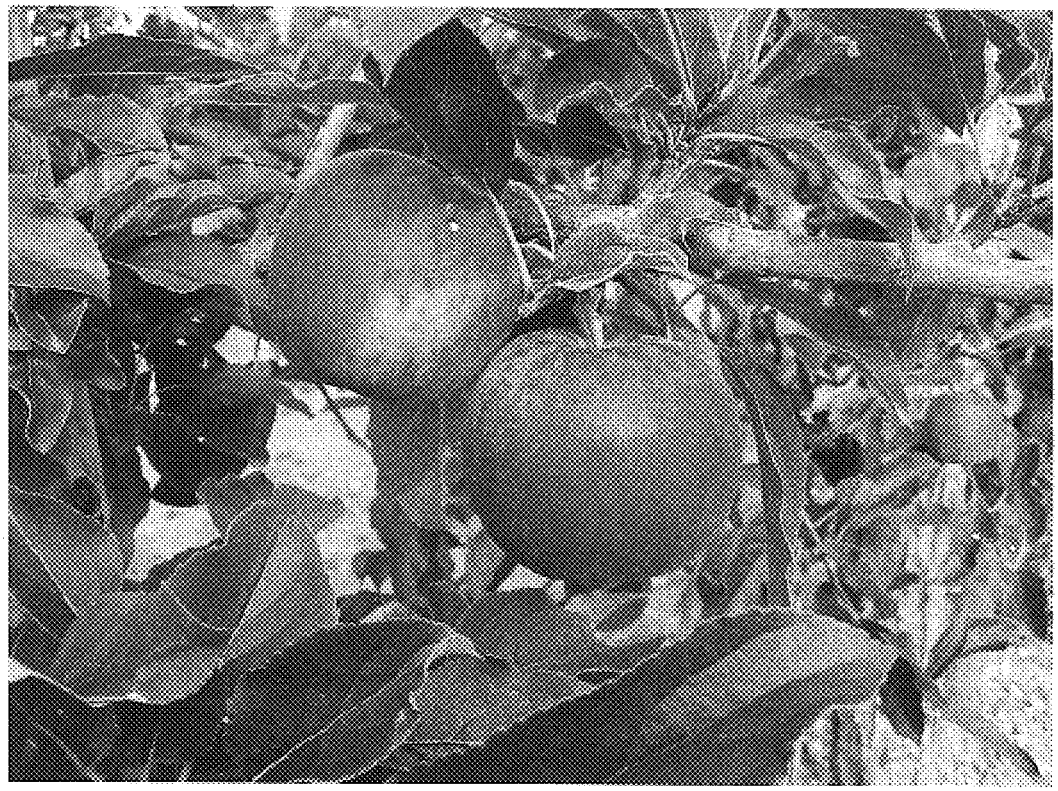
FIG. 1 shows the fruit and leaves of 'Dalitoga.'
Figure 2:
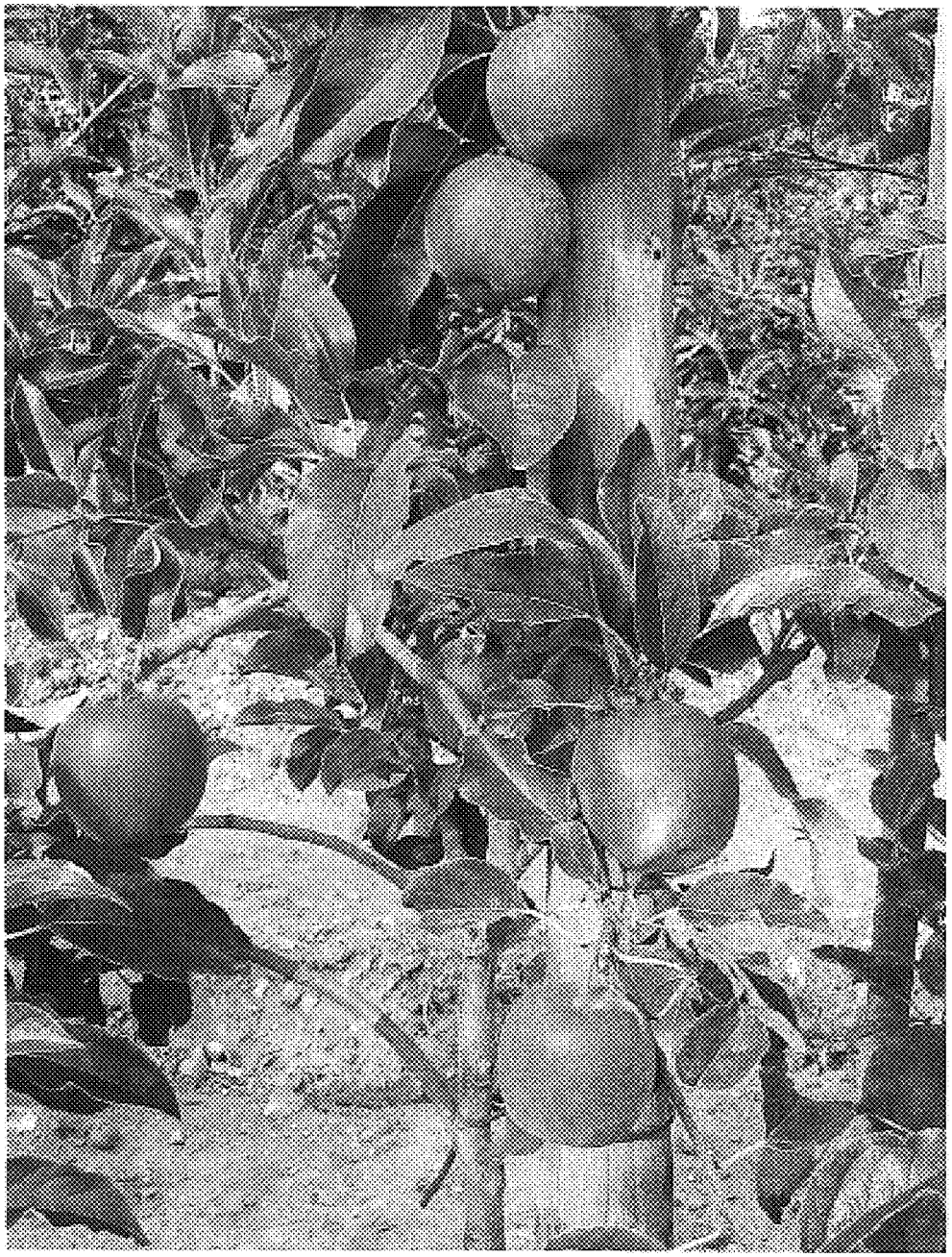
FIG. 2 shows the fruit, leaves and trunk of 'Dalitoga.'
Figure 3:
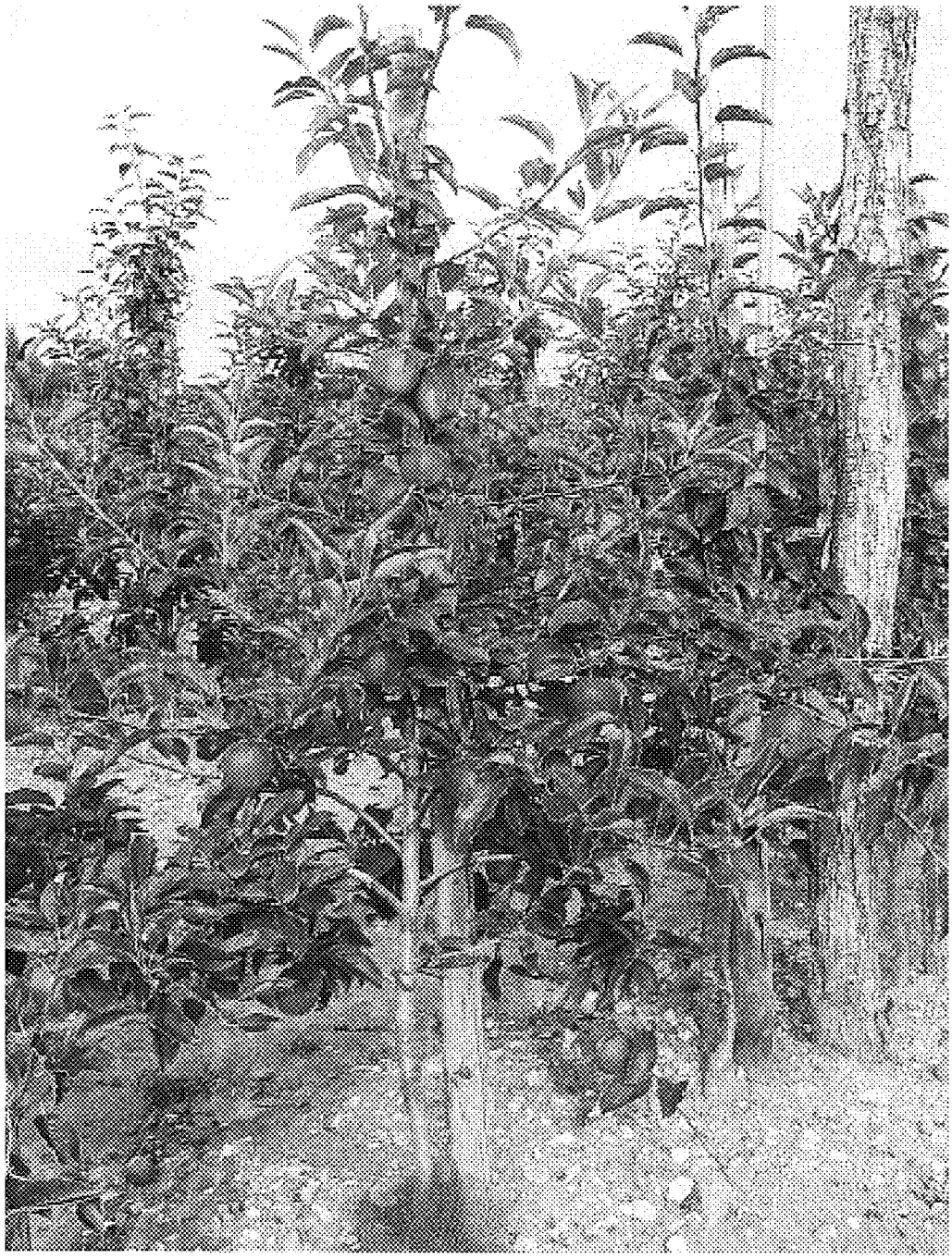
FIG. 3 shows the 'Dalitoga' tree.
Figure 4:
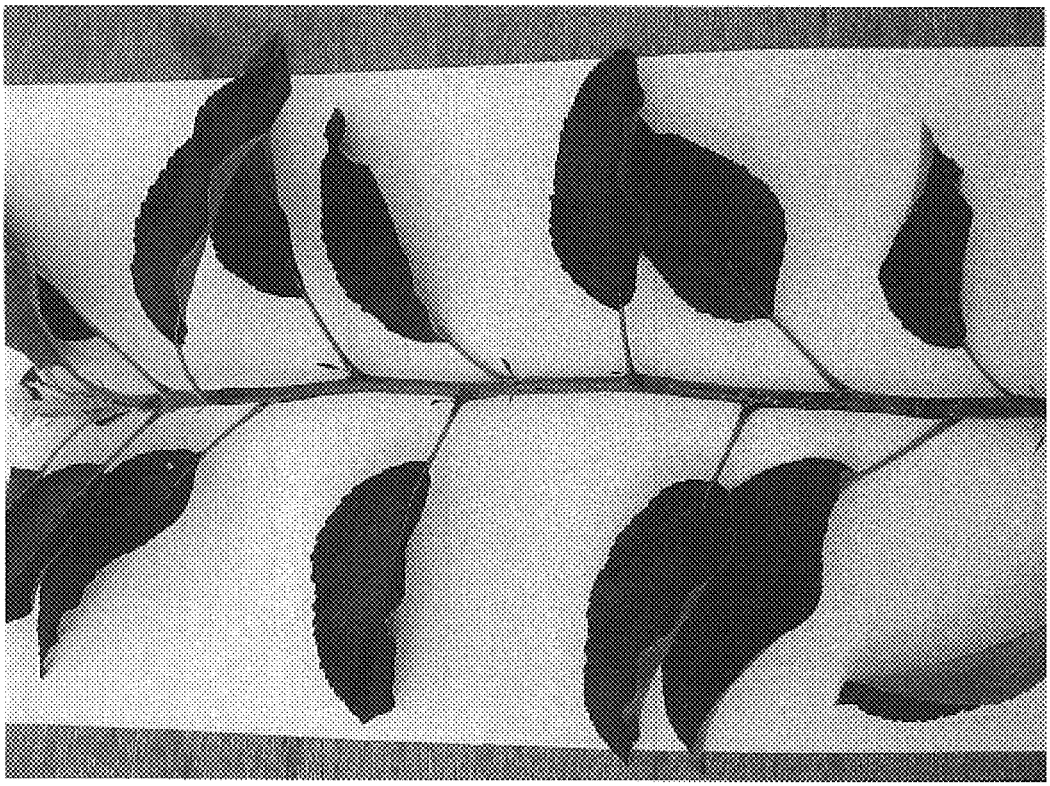
FIG. 4 shows a branch and leaves (1 year old shoot) of 'Dalitoga.'
Figure 5:
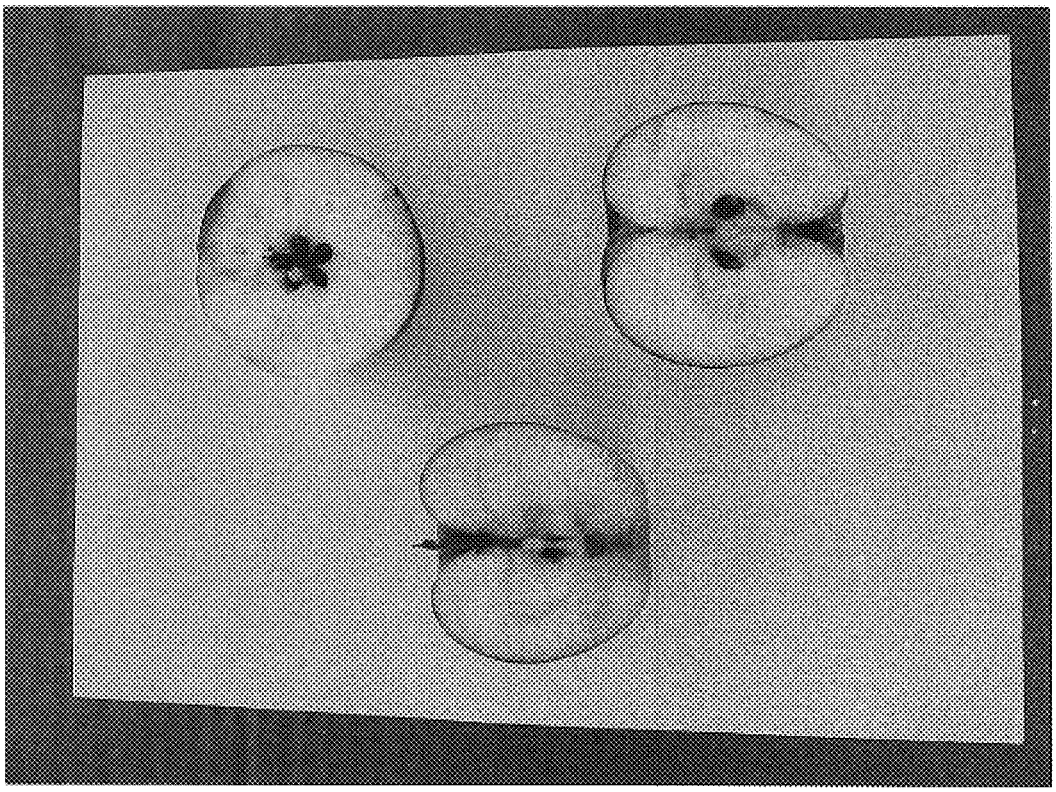
FIG. 5 shows the flesh of fruit of 'Dalitoga.'
Figure 6:
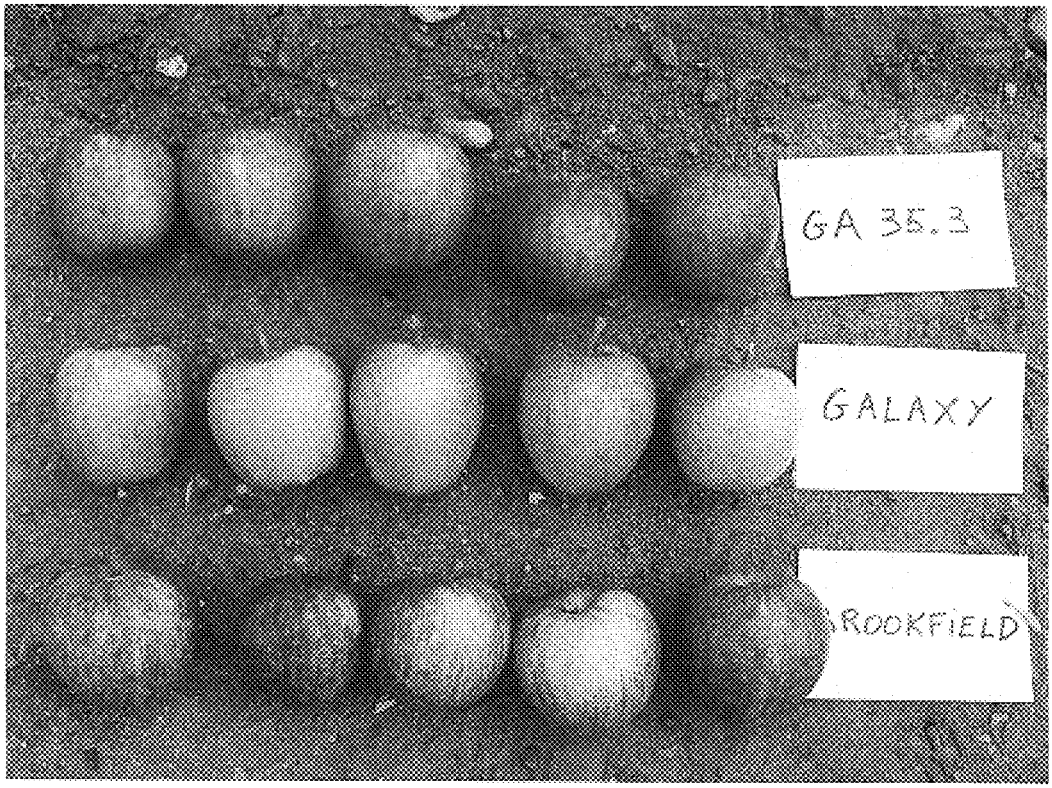

FIG. 6 shows 'Dalitoga' as compared with 'Galaxy' Gala (U.S. Plant Pat. No. 6,955) and Brookfield® 'Baigent' Gala (U.S. Plant Pat. No. 10,016).

Figure 7:
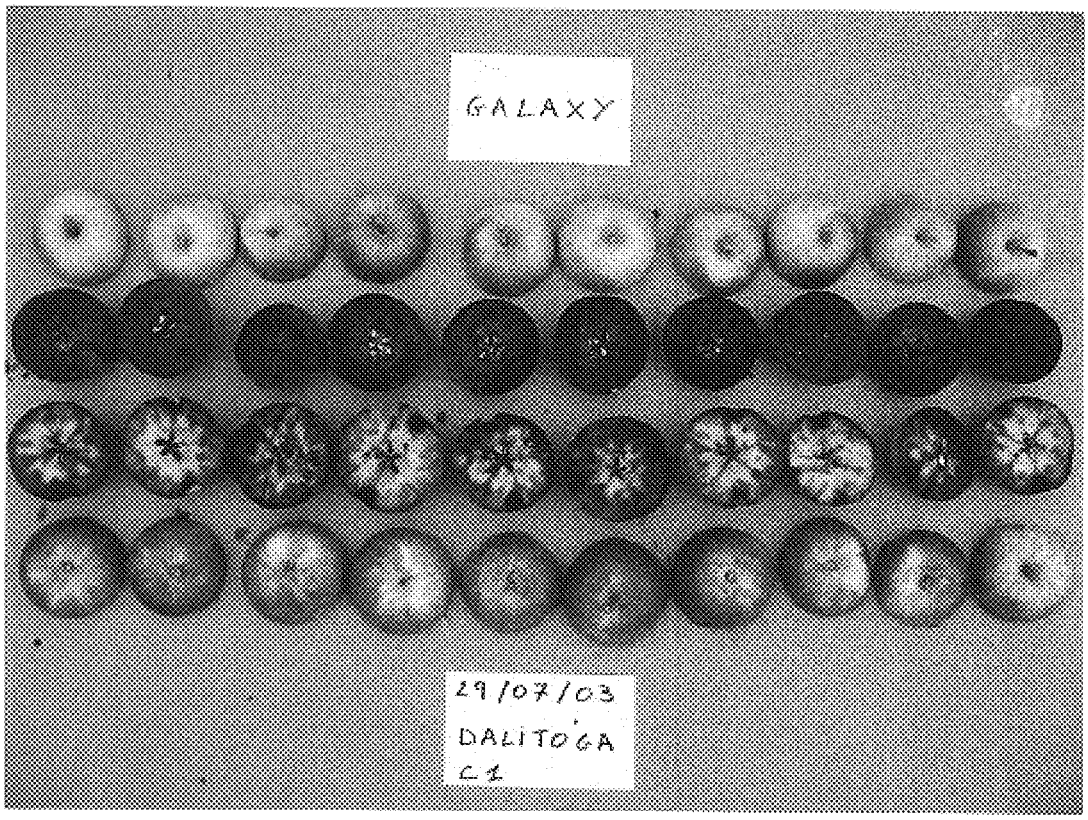

FIG. 7 shows the difference in maturity time between 'Dalitoga' and 'Galaxy' Gala with a comparison between the starch leaves, foreground and background colors of the two varieties picked on the same day.

BRIEF DESCRIPTION OF THE VARIETY

'Dalitoga' is a whole tree mutation of 'Imperial Gala' (not patented). The original mutation was discovered in 1998 in a cultivated block of 'Imperial Gala' trees near Lezigne, France, and was asexually propagated for testing purposes by budding at Doue La Fontaine, France in 1999 under breeder's reference number R25 A35-GA 35.3. Asexually propagated progeny of 'Dalitoga' have been found to retain the unique characteristics of the original 'Dalitoga' tree, and remain true to type through successive generations of asexual propagation.

'Dalitoga' is similar to its parent in terms of tree shape, vigor, and productivity. However, 'Dalitoga' is distinguishable from its parent in several respects, as summarized in Table 1:

TABLE 1

Comparison of 'Dalitoga' to 'Imperial Gala'

| Characteristic | Imperial Gala | 'Dalitoga' |
|---|---|---|
| Date of full bloom | Typical for Gala (compare to 'Galaxy') | 1–3 days earlier |
| Rate of fruit growth | Typical for Gala (compare to 'Galaxy') | 4 mm–8 mm larger than 'Imperial Gala' by mid-July |
| Coloration | 30% to 50% colored | 50% to 95% colored (avg. 75%) |
| Maturity | Last week of August | First week of August |

DETAILED BOTANICAL DESCRIPTION OF THE VARIETY

The following is a detailed botanical description of 'Dalitoga,' a new and distinct cultivar of *Malus pumila* Mill., based on observations made on the original tree from 1998 to 2001, and during the 2002, 2003, and 2004 growing seasons of specimens of the second generation planted at Angers, France in 2001 and 2002. All colors are described according to The Royal Horticultural Society Colour Chart. It should be understood that the botanical and analytical characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

1. Tree:
   *Vigor.*—Medium, similar to 'Imperial Gala'.
   *Type.*—Ramified.
   *Habit.*—Spreading.
   *Size.*—Height, 2.3 m; diameter, 1.3 m.
   *Trunk.*—Diameter 4.4 cm to 30 cm above graft union; bark medium-smooth, Grey-Brown N199A.
   *Branches.*—Length 65 cm; diameter 1.2 cm; crotch angle 60° to 80°, Brown 200B (based on fruiting branches located about 1.5 m above graft union).
   *Winter hardiness.*—Similar to 'Imperial Gala'.
   *Chilling requirement.*—Similar to 'Imperial Gala'.
2. Dormant one year old shoot:
   *Pubescence.*—Weak.
   *Size.*—Diameter 48 mm; length 20 to 40 cm.
   *Color.*—Green 143A.
   *Internode length.*—Long (avg. 26 mm).
   *Number of lenticels.*—Medium (avg. 9/cm$^2$).
3. Flowers:
   *Bud.*—1 to 3 per spur; round to conical; length 1.1 cm; diameter 1.2 cm; Red-Purple 60A.
   *Flower color* (*balloon stage*).—Red Purple from 73A to 74B.
   *Flower size.*—Diameter 38 cm; depth 1.3 cm; 5 to 6 per cluster.
   *Petals.*—5 per flower; slightly overlapping; length 1.7 cm; width 1.3 cm; round apex; conical-pointed base; smooth margin; upper surface White N155C; lower surface White N155B when fully open.
   *Sepals.*—5 per flower; conical pointed; length 7.9 mm; Green 143C.
   *Pedicel.*—Length medium to long, 2.2 cm; diameter quite thin, 1.4 mm; Green 143B.
   *Pistil.*—Length 1.3 cm; Yellow Green N144C.
   *Anthers.*—Numerous, avg. 13 per flower; 0.21 cm long; pollen Yellow 3C.
   *Stigma.*—Small to medium size, avg. 0.6 mm; Yellow Green 150B.
   *Style.*—Long, avg. 1.1 cm; Yellow Green 145A.
   *Ovary.*—Medium size, avg. 0.2 cm; Green 140A.
   *Bloom period.*—First bloom April 15 in Angers, France (1 to 2 days before 'Imperial Gala'); full bloom April 20 in Angers, France (1 to 2 days before 'Imperial Gala').
4. Leaf:
   *Attitude in relation to shoot.*—Outward (horizontal).
5. Leaf blade:
   *Length.*—Medium (avg. 89 mm).
   *Width.*—Medium (avg. 47 mm).
   *Length-width ratio.*—Medium.
   *Margin.*—Serrate.
   *Shape.*—Oval; acuminate tip; oblique base.
   *Color.*—Upper surface Green 137A; lower surface Yellow-Green 146B.
6. Petiole: Length medium to long, avg. 27 mm; diameter 2 mm; color Yellow-Green 144B.
7. Fruit:
   *Size.*—Medium (avg. 67.5 mm; 119 g).
   *Ratio of height to width.*—Medium to large.
   *General shape in profile.*—Oblong to oblong conical.
   *Position of maximum diameter.*—Middle.
   *Ribbing.*—Weak.
   *Crowning at calyx end.*—Weak.
   *Aperture of eye.*—Closed.
   *Size of eye.*—Small (avg. 9.4 mm).
   *Depth of eye basin.*—Medium (avg. 7.9 mm).
   *Width of eye basin.*—Medium (avg. 27.4 mm).
   *Stalk.*—Diameter medium (avg. 3.7 mm); Length short to medium (avg. 16.3 mm); Grey-Brown N199C.
   *Depth of stalk cavity.*—Medium to deep (avg. 11.8 mm).
   *Width of stalk cavity.*—Medium (avg. 31.5 mm).
   *Size of lenticels.*—Small (avg. 0.7 mm).
   *Bloom of skin.*—Weak.
   *Greasiness of skin.*—Very weak.
   *Ground color of skin.*—Yellow-Green 154C to Yellow 4C.
   *Over color of skin.*—Red 46B Red Orange 34A.
   *Amount of over color.*—High.
   *Intensity of over color.*—Medium.
   *Pattern of over color.*—50% to 95% stripes (avg. 75%) with solid flush in some parts.
   *Flesh.*—Medium to fine texture; very juicy; Yellow-White 158D.
   *Seeds.*—11 per fruit; ovoid; Brown 200B.
   *Quantity per cluster.*—3 to 4 fruits per cluster.
   *Aroma.*—Slightly more intense than 'Imperial Gala'.
   *Yield.*—80 fruits per tree in 4$^{th}$ leaf under growing conditions in Angers, France.

TABLE 2

Quantitative analysis of fruit

| | DALITOGA (First picking, 29 July 2003) | | | |
|---|---|---|---|---|
| Fruits | Pressure 1 (kg/cm$^2$) | Pressure 2 (kg/cm$^2$) | Sugar (Brix) | Starch 0 to 10 |
| 1 | 8.6 | 8.1 | 12.8 | 4 |
| 2 | 8.8 | 8.7 | 11.8 | 5 |
| 3 | 9.8 | 9.5 | 12.6 | 3 |
| 4 | 8.5 | 7.2 | 14 | 6 |
| 5 | 9.7 | 8 | 12.4 | 5 |
| 6 | 8.1 | 9.2 | 12.6 | 3 |
| 7 | 7.8 | 7.4 | 14.2 | 5 |
| 8 | 7.8 | 6.6 | 13 | 7 |
| 9 | 10.3 | 10.1 | 12 | 3 |
| 10 | 7.8 | 7.7 | 13.6 | 5 |
| Avg. | 8.72 | 8.25 | 12.9 | 4.6 |

*Use.*—Fresh market.
   *Resistance to known diseases.*—None noted.
   *Storageability.*—Good; in limited early trials, fruit retained firmness, taste and texture after three months in real atmosphere storage.

We claim:

1. A new and distinct apple tree, substantially as shown and described herein.

* * * * *